United States Patent
Marra

(10) Patent No.: US 8,402,815 B2
(45) Date of Patent: Mar. 26, 2013

(54) AIR POLLUTION SENSOR SYSTEM

(75) Inventor: Johan Marra, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 514 days.

(21) Appl. No.: 12/593,933

(22) PCT Filed: Apr. 3, 2008

(86) PCT No.: PCT/IB2008/051244
§ 371 (c)(1),
(2), (4) Date: Sep. 30, 2009

(87) PCT Pub. No.: WO2008/122932
PCT Pub. Date: Oct. 16, 2008

(65) Prior Publication Data
US 2010/0107739 A1    May 6, 2010

(30) Foreign Application Priority Data
Apr. 6, 2007 (EP) .................................. 07105834

(51) Int. Cl.
*G01N 1/00* (2006.01)
(52) U.S. Cl. ...................................... 73/28.04
(58) Field of Classification Search .............. 73/28.04, 73/28.01, 28.02, 28.03
See application file for complete search history.

(56) References Cited

U.S. PATENT DOCUMENTS

| | | | | |
|---|---|---|---|---|
| 3,826,180 A * | 7/1974 | Hayashi | ....................... | 454/342 |
| 5,279,731 A | 1/1994 | Cook et al. | | |
| 5,825,487 A | 10/1998 | Felbinger et al. | | |
| 6,611,611 B2 | 8/2003 | Oka et al. | | |
| 2005/0126260 A1* | 6/2005 | Totoki | ........................... | 73/31.02 |
| 2005/0229777 A1 | 10/2005 | Brown et al. | | |
| 2005/0241417 A1 | 11/2005 | Kay | | |
| 2007/0012181 A1* | 1/2007 | Niezgoda et al. | .................... | 95/1 |

FOREIGN PATENT DOCUMENTS

| | | |
|---|---|---|
| DE | 4105598 A1 | 8/1992 |
| WO | 2006016345 A1 | 2/2006 |
| WO | 2006016346 A1 | 2/2006 |
| WO | WO 2006/016345 * | 2/2006 |

* cited by examiner

*Primary Examiner* — Hezron E Williams
*Assistant Examiner* — Nathaniel Kolb
(74) *Attorney, Agent, or Firm* — Larry Liberchuk

(57) ABSTRACT

The invention relates to an air pollution sensor system (1) comprising an air inlet (11), an air outlet (12), a sensor unit (2), and an air displacement device (3). The air displacement device is arranged to establish an air flow (4) from the air inlet through the sensor unit to the air outlet. The sensor unit comprises, a filter (22) for removing airborne pollutants from the air flow. The sensor unit is arranged to generate an output signal (21) based on the amount of airborne pollutants removed from the air flow by the filter. The air displacement device is arranged to be controlled by the output signal, thereby improving the lifetime of the air pollution sensor system by minimizing the amount of pollutants that will be deposited inside the sensor unit when the air pollution sensor system is operated under predetermined conditions.

12 Claims, 6 Drawing Sheets

AIR POLLUTION SENSOR SYSTEM

FIELD OF THE INVENTION

The invention relates to an air pollution sensor system comprising an air inlet, an air outlet, a sensor unit, and an air displacement device, the air displacement device being arranged to establish an air flow from the air inlet through the sensor unit to the air outlet, the sensor unit comprising a filter for removing airborne pollutants from the air flow, the sensor unit being arranged to generate an output signal based on the amount of airborne pollutants removed from the air flow by the filter.

BACKGROUND OF THE INVENTION

An air pollution sensor system is used for monitoring the concentration of airborne pollutants, particularly of health-hazardous airborne pollutants. In combination with a filtration system comprised in an air handling system, an air pollution sensor system can be used to monitor and control the concentration of airborne pollutants inside an enclosure receiving ventilation air from the air handling system.

An air pollution sensor system comprises an air inlet, an air outlet, a sensor unit, and an air displacement device, the air displacement device being arranged to establish an air flow from the air inlet through the sensor unit to the air outlet. The sensor unit functions through interaction with airborne pollutants, for instance by removing airborne pollutants from the air flow using a filter, or by determining the presence of airborne pollutants in the air flow by interaction with electromagnetic radiation.

The sensor unit of the air pollution sensor system according to the invention comprises a filter for removing airborne pollutants from the air flow. As a result, the sensor unit generates an output signal with a magnitude that is proportional to the amount of airborne pollutants that is removed by the filter per unit time.

During operation an increasing amount of airborne pollutants is being deposited in the sensor unit. Consequently, the magnitude of the output signal measured at a certain air pollution level may change over time, for instance because of changing filter or filtration characteristics. The lifetime of an air pollution sensor system is defined as the time after which the magnitude of the output signal measured under a defined set of conditions has changed to a certain percentage (for instance 50%) with respect to the initially measured value in the presence of a clean filter.

An air pollution sensor system comprising a sensor unit and a ventilator for displacing air is known from WO 2006/016346 A1. The sensor unit of the known air pollution sensor system comprises a particle precipitation section. With respect to maintenance issues and the reliability of the output signal, there is an ongoing need to improve the lifetime of such an air pollution sensor system.

SUMMARY OF THE INVENTION

It is an object of the invention to provide an air pollution sensor system of the kind set forth in the opening paragraph that has an improved lifetime.

According to the invention this object is realized in that the air displacement device is arranged to be controlled by the output signal.

To improve the lifetime of an air pollution sensor system of the kind set forth in the opening paragraph, it is important to ensure that during operation the rate and amount of deposition of airborne pollutants inside the sensor unit is as low as possible. When the output signal of the sensor unit is used as a feedback signal to control the air displacement device, the air flow through the sensor unit can for instance be reduced when the output signal exceeds a certain predetermined value. This reduces the rate of deposition of airborne pollutants in the sensor unit, thereby extending the lifetime of the air pollution sensor system.

An embodiment of the air pollution sensor system of the invention is defined in claim 2. In this embodiment the air displacement device is arranged to adjust the air flow to have a reduced volumetric flow rate when the output signal exceeds a first predetermined value. This embodiment further increases the lifetime of the air pollution sensor system because a reduced amount of airborne pollutants will deposit inside the sensor unit during the period of time wherein the air flow has a reduced volumetric flow rate.

An embodiment of the air pollution sensor system of the invention is defined in claim 3. In this embodiment the air displacement device is arranged to adjust the air flow to have a reduced volumetric flow rate when the output signal falls below a second predetermined value. This embodiment further increases the lifetime of the air pollution sensor system because a reduced amount of airborne pollutants will deposit inside the sensor unit during the period of time wherein the air flow has a reduced volumetric flow rate.

An embodiment of the air pollution sensor system of the invention is defined in claim 4. In this embodiment the air displacement device is arranged to reduce the volumetric flow rate of the air flow to zero for a predetermined period of time when the output signal either exceeds a first predetermined value, or when the output signal falls below a second predetermined value. This embodiment further increases the lifetime of the air pollution sensor system because no airborne pollutants will deposit inside the sensor unit during the predetermined period of time.

An embodiment of the air pollution sensor system of the invention is defined in claim 5. In this embodiment the output signal is reset to zero during the predetermined period of time wherein the volumetric flow rate of the air flow is reduced to zero, thereby increasing the reliability and reproducibility of the output signal and consequently the lifetime of the air pollution sensor system. When there is no air flow through the air pollution sensor system, no pollutants can deposit inside the sensor unit and the output signal should be zero by definition. Any possibly existing non-zero offset value in the output signal can then be compensated via a zero reset.

An embodiment of the air pollution sensor system of the invention is defined in claim 6. In this embodiment the filter is an air-permeable depth filter. This embodiment further increases the lifetime of the air pollution sensor system as it raises the maximum amount of pollutant mass that is allowed to be deposited in the sensor unit before the filter or filtration characteristics will significantly change in response to the mass of pollutants that is deposited inside the filter.

An embodiment of the air pollution sensor system of the invention is defined in claim 7. In this embodiment, the air pollution sensor system comprises an arrangement for causing the air flow to follow a curved path between the air inlet and the sensor unit. This embodiment further increases the lifetime of the air pollution sensor system as it prevents large airborne particles, for which the sensor might have a low sensitivity, to reach the filter and thus from being deposited in the filter.

An embodiment of the air pollution sensor system of the invention is defined in claim 8. In this embodiment, the air pollution sensor system comprises a heating element that is arranged to reduce the relative humidity of at least a part of the air flow. This embodiment further increases the lifetime of the air pollution sensor system as it reduces adsorption and/or condensation of moisture in the interior of the sensor unit, thereby preventing the occurrence of an undesirable electrical current.

These and other aspects of the invention will be apparent from and elucidated with reference to the embodiments described hereinafter.

BRIEF DESCRIPTION OF THE DRAWINGS

Examples of the invention will now be described in detail with reference to the accompanying drawings, in which.

Figure 1:
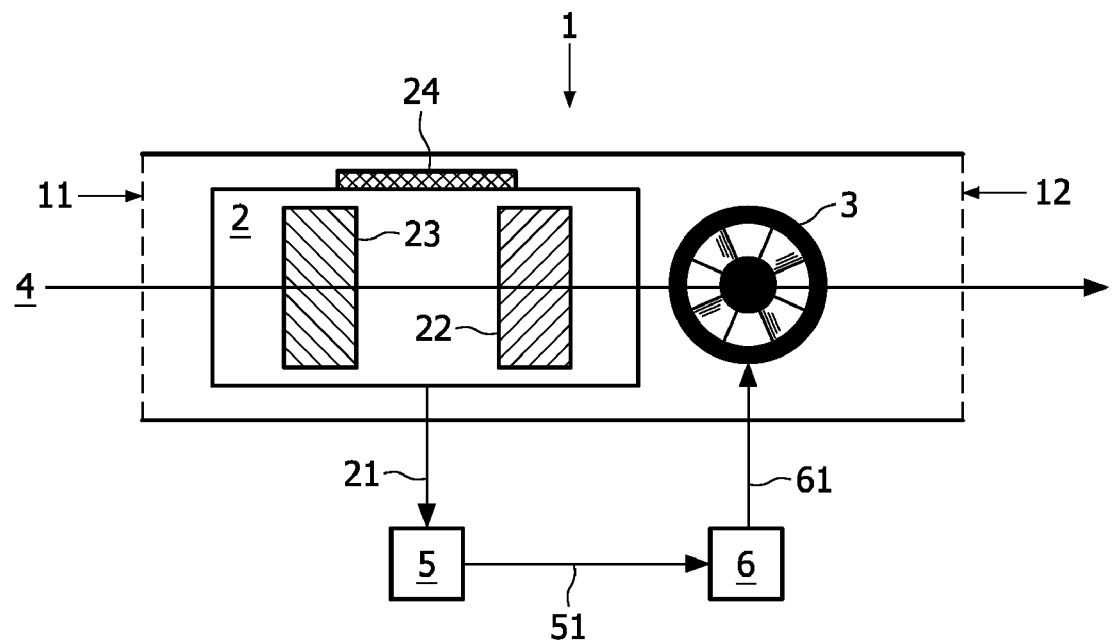
FIG. 1 is a schematic representation of a first embodiment of the air pollution sensor system according to the invention.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION OF THE EMBODIMENTS

The air pollution sensor system 1 of FIG. 1 comprises an air inlet 11, an air outlet 12, a sensor unit 2, and a fan 3. For the purpose of the invention, the fan 3 can be replaced by any other air displacement device, such as a pump or a heating element that is arranged to displace air by means of a thermal chimney effect caused by local differences in air density. When in operation, the fan 3 creates a pressure drop across the sensor unit 2, thereby establishing an air flow 4 through the sensor unit 2, the volumetric flow rate of which is determined by the rotational speed of the fan 3. The volumetric flow rate indicates the volume of air which passes trough a given volume per unit time.

In FIG. 1, the sensor unit 2 is a particle sensor unit that is arranged to sense the presence of airborne particles in the air flow 4. For this purpose, the sensor unit 2 comprises an air-permeable depth filter 22 that is arranged to remove electrically-charged particles from the air flow 4. The electrically-charged particles are created by a particle charging unit 23 that is comprised in the sensor unit 2, and positioned between the air inlet 11 and the filter 22.

For the purpose of the invention, a sensor unit can be any device that is arranged to sense the presence of airborne pollutants, provided that its sensing function involves the removal of pollutants from an air flow by a filter. In the context of this invention, the filter can be any device that is arranged to remove airborne pollutants from an air flow.

During operation of the air pollution sensor system 1, an increasing amount of particle mass is being deposited in the filter 22. As a result, the air flow resistance of the filter 22 increases, thereby reducing the volumetric flow rate of the air flow 4 that exists at a certain fan-induced driving force for the air flow.

In FIG. 1, the filter 22 is an air-permeable depth filter with a thickness of at least several mm. As a result, the air flow resistance of the filter 22 is less sensitive towards the deposited particle mass. Consequently, the filter 22 is able to remove a relatively larger particle mass from the air flow 4 before the air flow resistance of the filter is increased to such an extent that the volumetric flow rate of the air flow 4 is reduced to a degree that the sensor unit 2 is no longer able to provide a sufficiently reliable output signal.

The sensor unit 2 is arranged to generate an output signal 21 based on the presence of airborne particles in the air flow 4. The magnitude of the output signal 21 depends on the amount of particles that is removed from the air flow 4 by the filter 22 per unit time. The output signal 21 is processed by a data evaluation unit 5. The data evaluation unit 5 is arranged to generate a feedback signal 51 based on the output signal 21. The controller 6 is arranged to process the feedback signal 51. The fan 3 is arranged to be controlled by the controller 6 via a voltage 61.

The output signal 21 is directly proportional to the volumetric flow rate of the air flow 4. As the volumetric flow rate is influenced by the voltage 61 that is supplied to the fan 3, the output signal 21 will be dependent on the magnitude of the voltage 61. The interpretation of the output signal 21 measured at different voltages 61 may be simplified by automatically compensating the output signal 21 for differences in the air flow 4 as induced by different voltages 61. For this purpose, the data evaluation unit 5 may comprise a compensation algorithm.

The air pollution sensor system 1 of FIG. 1 comprises a heating element 24 that is positioned in contact with the sensor unit 2. The heating element 24 is arranged to reduce the relative humidity of air in order to reduce adsorption and/or condensation of moisture in the interior of the sensor unit 2. Consequently, the occurrence of an undesirable electrical current, such as an electrical current flowing along an insulative surface of the interior of the sensor unit 2, will be prevented, thereby improving the performance of the air pollution sensor system 1 with respect to lifetime, measurement accuracy, and measurement reliability. The heating element 24 may be a resistive heating element, and may also be positioned in close proximity of the sensor unit 2.

Figure 2A:
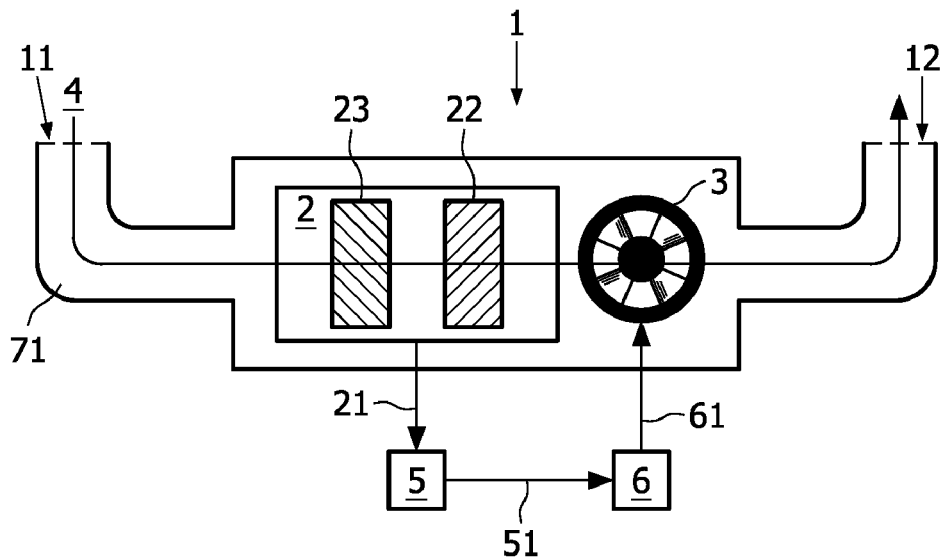
FIGS. 2A-2C are schematic representations of further embodiments of the air pollution sensor system according to the invention.
Figure 2B:
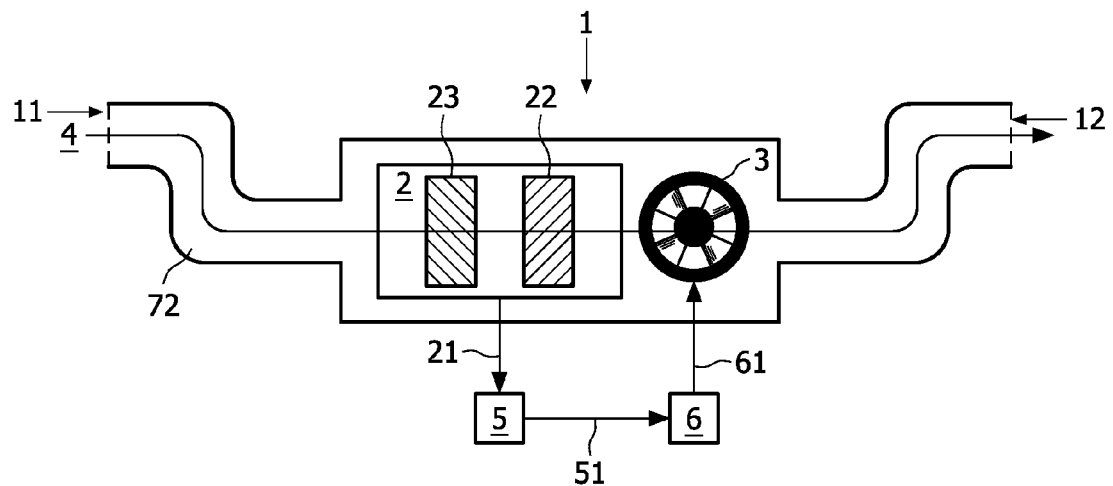
Figure 2C:
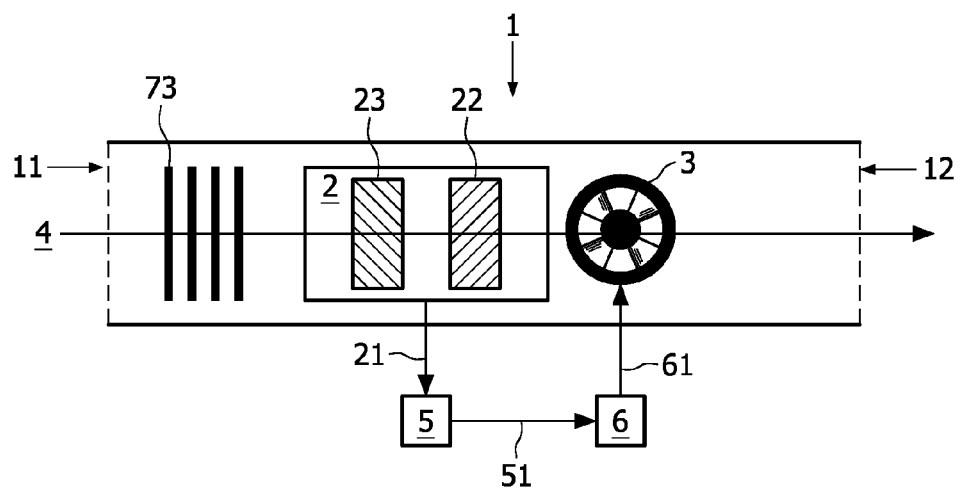

FIG. 2 shows embodiments of the air pollution system 1 that comprise an arrangement for causing the air flow 4 to follow a curved path between the air inlet 11 and the sensor unit 2. In FIGS. 2A and 2B, the arrangement is a curved air duct 71 and 72, respectively. In FIG. 2C, the arrangement is a plurality of parallel plates 73, the surface of which is oriented perpendicular to the air flow 4. In the embodiment of FIG. 2C, the air flow 4 is forced to traverse a zig-zag path between the parallel plates 73 before reaching the sensor unit 2. Concerning the part where the air flow 4 leaves the air pollution sensor system 1, (i.e. the part between the air displacement device 3 and the air outlet 12) this can be constructed in any way so as to direct the air flow 4 in a desired direction.

The embodiments shown in FIG. 2A-C prevent the entrance of relatively large airborne particles into the sensor unit 2, as a result of particle removal from the air flow 4 through particle deposition upstream of the sensor unit 2 caused by either inertial effects or by gravity effects. This is particularly useful when the sensor unit 2 is specifically arranged to be responsive towards particles with an equivalent diameter within a specified range, for instance when the sensor unit 2 is an ultrafine-particle sensor. Ultrafine particles are particles with an equivalent diameter between about 10 nm and about 2.5 μm. An ultrafine particle sensor has a relatively low sensitivity for large airborne particles at concentrations typically encountered in ambient air. Such large airborne particles can be prevented from depositing in the filter 22 because their tendency to deposit from the air flow 4 upstream of the filter 22, either through gravity sedimentation or inertial effects (collisions with solid surfaces followed by adhesive sticking), is relatively large.

In addition, when the air pollution sensor system 1 is used inside an air duct in which an external air flow can be established, the air inlet 11 can be properly positioned with respect to the direction of the external air flow so as force the air that is sampled from the external air flow by the air pollution sensor system 1 to make a substantial change in flow direction and/or flow rate before being able to enter the air pollution sensor system 1 via the air inlet 11. The change in flow direction and/or flow rate of the sampled air with respect to the external air flow also helps to prevent relatively large particles from entering the air pollution sensor system 1 due to hydrodynamic inertial effects.

Figure 3:
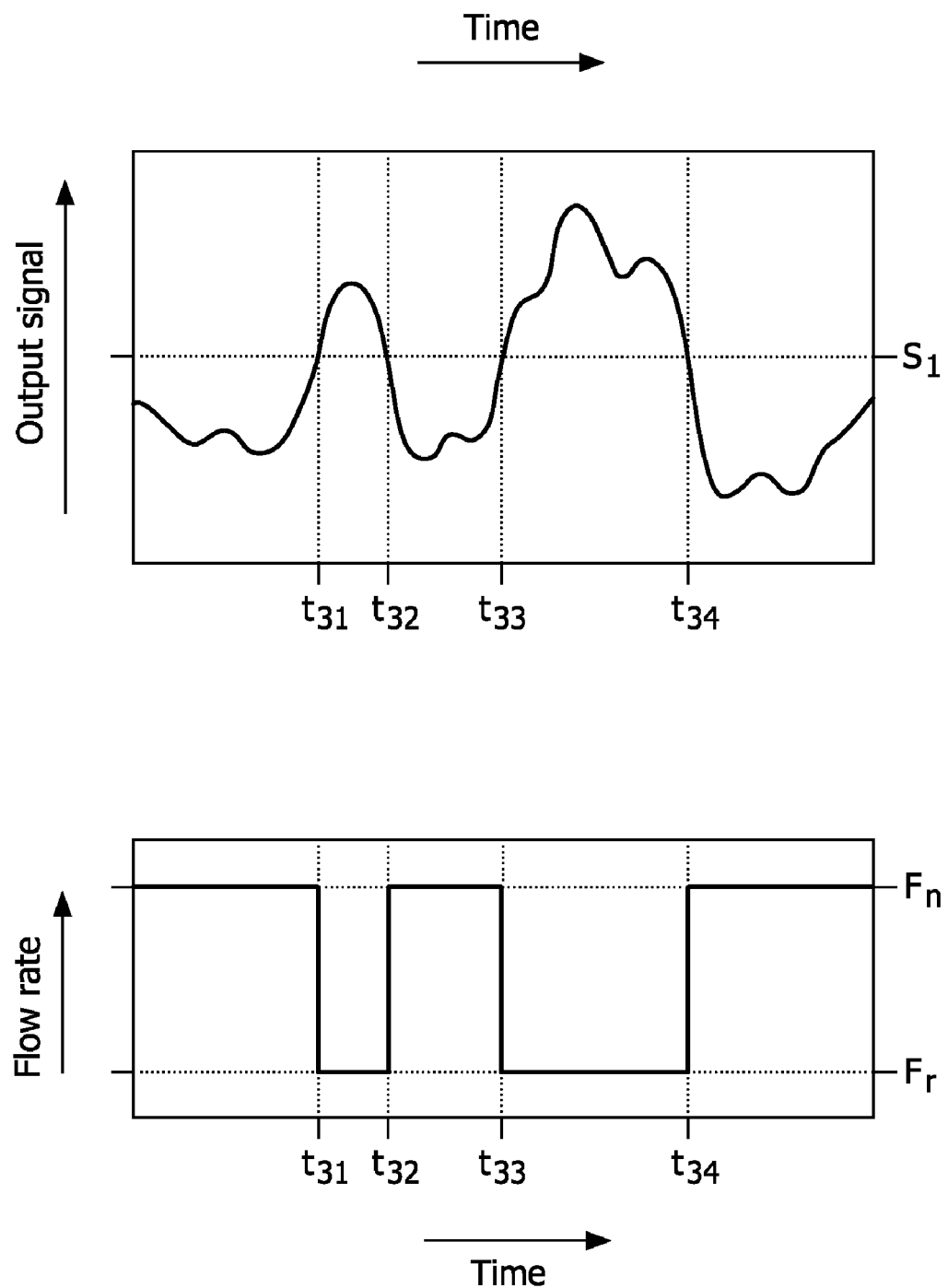
FIG. 3 graphically shows a first example of the operation of an embodiment of the air pollution sensor system 1.

FIG. 3 graphically shows an example of the operation of an embodiment of the air pollution sensor system 1. The upper graph of FIG. 3 shows an example of the output signal 21 as a function of time. A predetermined value $S_1$ is indicated in the upper graph. The voltage 61 supplied to the fan 3 is normally set at a nominal voltage so that a nominal air flow $F_n$ is established through the sensor unit 2. When the sensor signal 21 exceeds the predetermined value $S_1$, the feedback signal 51 is used to reduce the voltage 61 in order to reduce the rotational speed of the fan 3 thereby obtaining a reduced volumetric flow rate $F_r$, and consequently a reduced rate of pollutant deposition inside the filter 22. Such a feedback functionality extends the lifetime of the sensor unit 2.

The lower graph of FIG. 3 shows the volumetric flow rate of the air flow 4 as a function of time. At times $t_{31}$ and $t_{33}$, the output signal 21 exceeds the predetermined value $S_1$, and the volumetric flow rate of the air flow 4 is reduced from the nominal volumetric flow rate $F_n$ to the reduced volumetric flow rate $F_r$. The reduced volumetric flow rate $F_r$ can be a finite value or zero. In FIG. 3, the reduced volumetric flow rate $F_r$ is a finite value. In FIG. 3, the reduced volumetric flow rate $F_r$ is maintained until the output signal 21 falls below the predetermined value $S_1$, at which time ($t_{32}$ and $t_{34}$) the nominal volumetric flow rate $F_n$ is restored.

Figure 4:
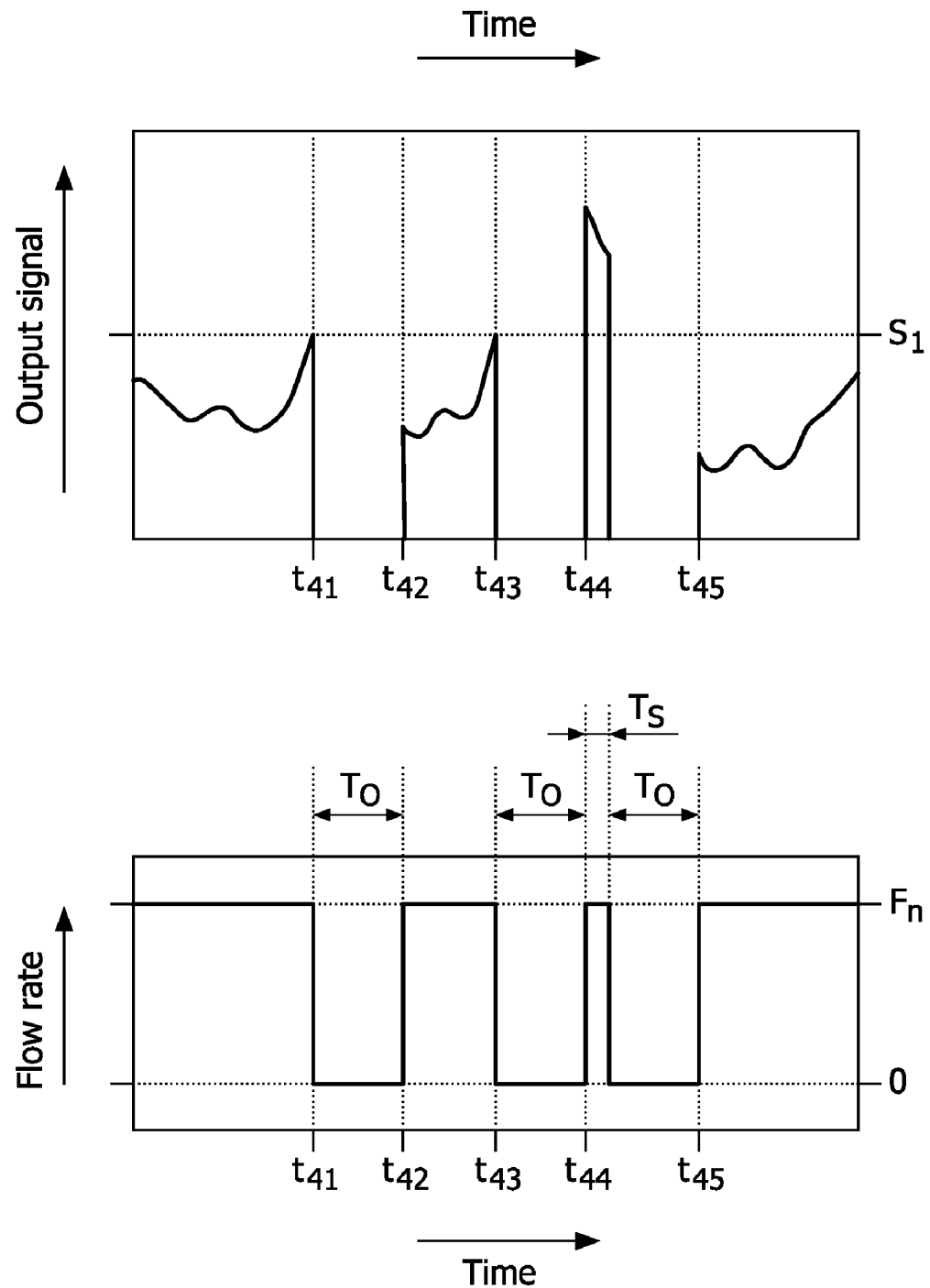
FIG. 4 graphically shows a second example of the operation of an embodiment of the air pollution sensor system 1.

FIG. 4 graphically shows an example of the operation of an embodiment of the air pollution sensor system 1 wherein the fan 3 is arranged to be switched off for a predetermined period of time $T_O$ when the output signal 21 exceeds the predetermined value $S_1$. At time $t_{41}$, the output signal 21 exceeds the predetermined value $S_1$, and the volumetric flow rate of the air flow 4 is reduced from the nominal volumetric flow rate $F_n$ to zero. The sensor unit 2 is not able to generate the output signal 21 when the air flow 4 is zero. Therefore, the nominal volumetric flow rate $F_n$ is restored after the predetermined period of time $T_O$ (during which period there is no output signal 21, as shown in the upper graph of FIG. 4). As during the predetermined period of time $T_O$, from $t_{41}$ to $t_{42}$, the concentration of airborne pollutants has decreased such that at $t_{42}$ the output signal 21 has a value lower than the first predetermined value $S_1$, the nominal volumetric flow rate $F_n$ is restored. At time $t_{43}$, the output signal 21 again exceeds the predetermined value $S_1$ and the volumetric flow rate is again reduced to zero. Following the predetermined period of time $T_O$, the nominal volumetric flow rate $F_n$ is restored at time $t_{44}$. However, at $t_{44}$ the output signal 21 still exceeds the predetermined value $S_1$, so that the volumetric flow rate is immediately reduced to zero (in practice, the sensor unit 2 requires a finite sampling time $T_S$ for producing the output signal 21). Following the predetermined period of time $T_O$, the nominal volumetric flow rate $F_n$ is restored at time $t_{45}$. Now the output signal 21 has decreased to a value lower than the predetermined value $S_1$ so that the nominal volumetric flow rate $F_n$ can be maintained.

Figure 5:
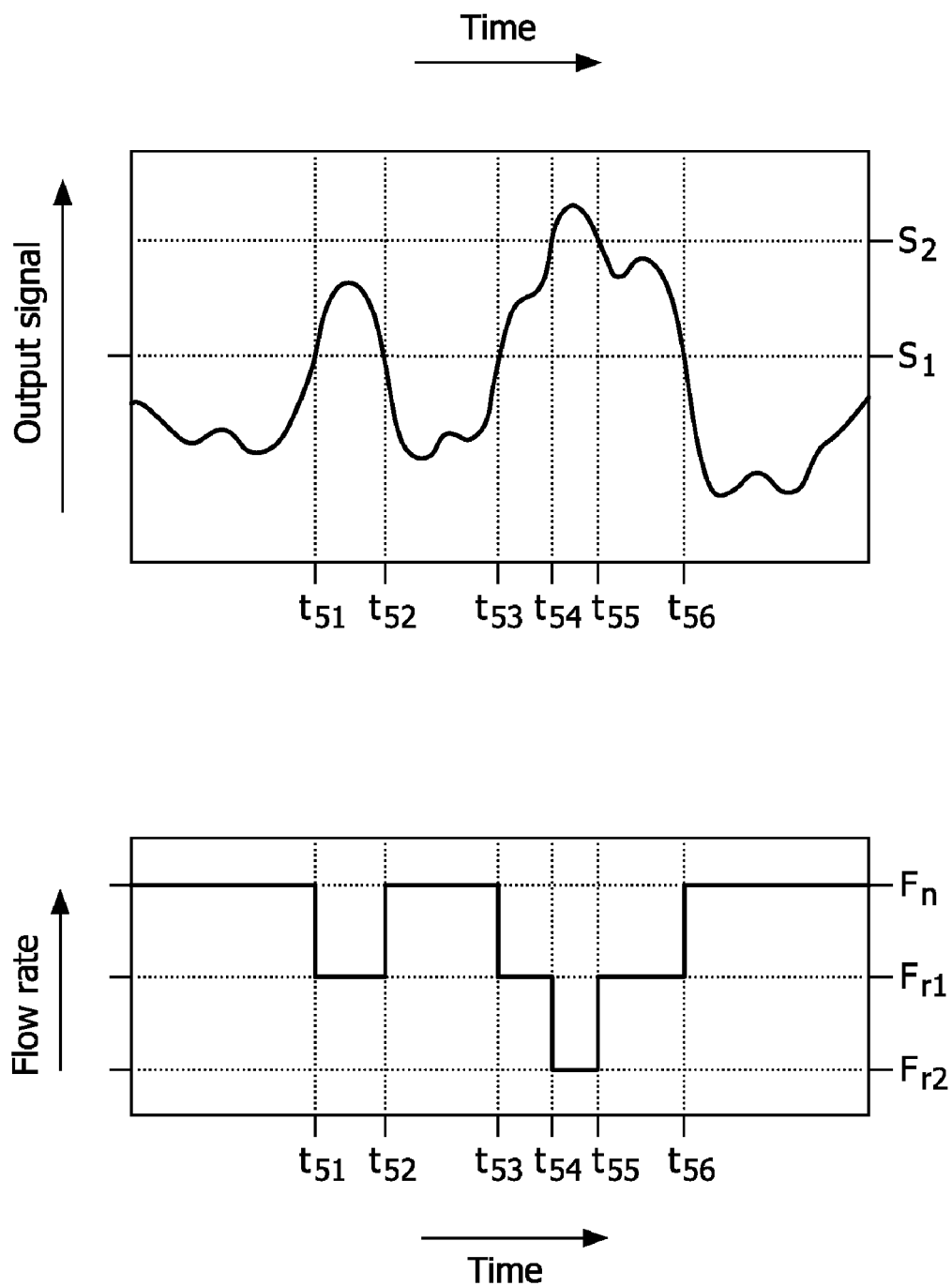
FIG. 5 graphically shows a third example of the operation of an embodiment of the air pollution sensor system 1.

In another embodiment of the air pollution sensor system 1, several predetermined values of the output signal 21 may be defined at which suitable reductions of the volumetric flow rate of the air flow 4 are to be effected. An example of the operation of such an embodiment is shown in FIG. 5. Similar to FIG. 3 and FIG. 4, the upper graph of FIG. 5 shows an example of the output signal 21 as a function of time. The lower graph of FIG. 5 shows the volumetric flow rate of the air flow 4 as a function of time. In FIG. 5, when the output signal 21 exceeds the first predetermined value $S_1$ (at times $t_{51}$ and $t_{53}$), the volumetric flow rate of the air flow 4 is reduced to a first finite reduced volumetric flow rate $F_{r1}$. When the output signal 21 subsequently exceeds the second predetermined value $S_2$ (at time $t_{54}$) the volumetric flow rate is further reduced to a second reduced volumetric flow rate $F_{r2}$. In FIG. 5, the second reduced volumetric flow rate $F_{r2}$ has a finite value, but it can also be zero.

Figure 6:
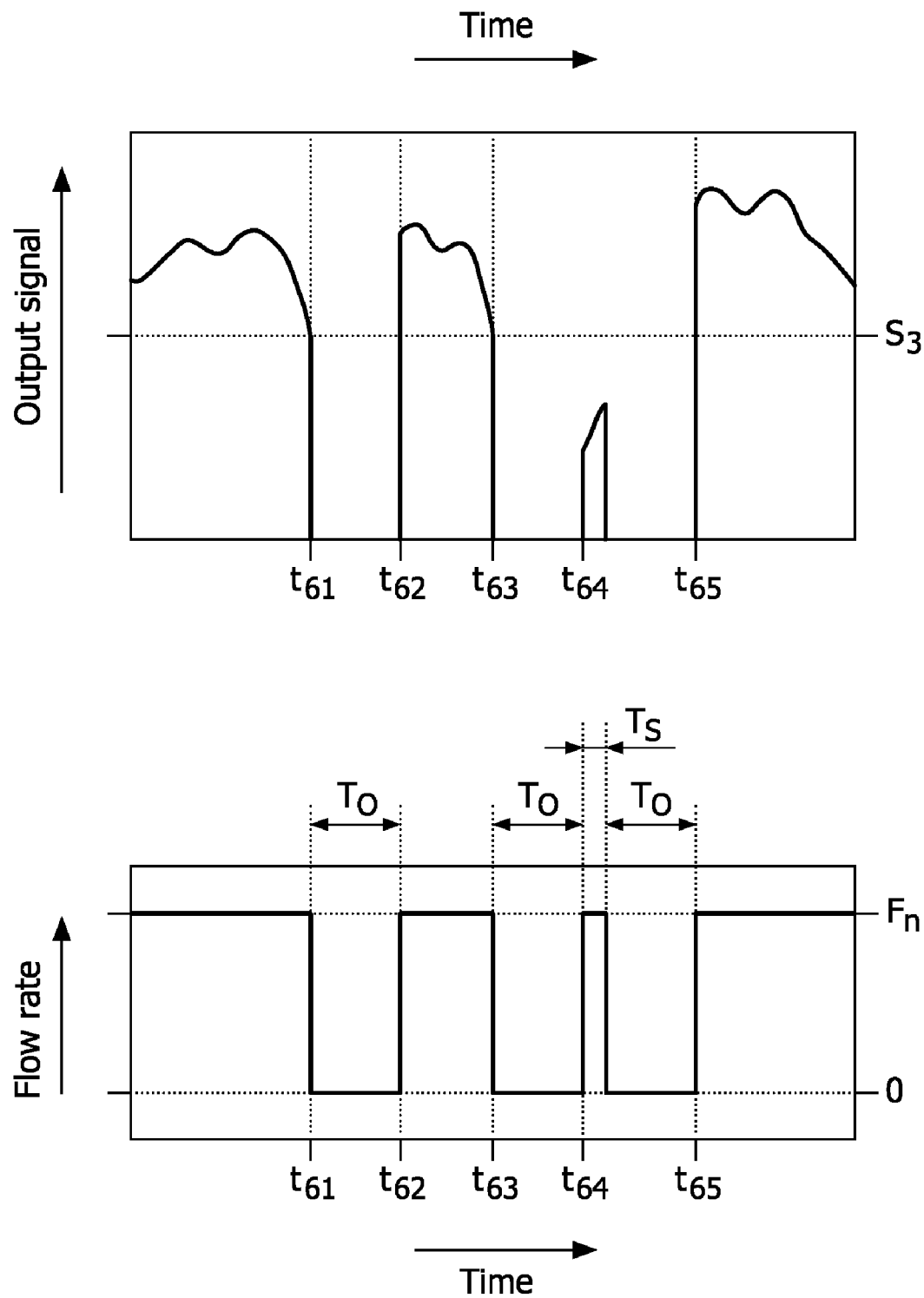
FIG. 6 graphically shows a fourth example of the operation of an embodiment of the air pollution sensor system 1.

In a further embodiment of the air pollution sensor system 1, the fan 3 can be arranged to be switched off for a predetermined period of time when the sensor signal 21 falls below a predetermined value. FIG. 6 graphically shows an example of the operation of such an embodiment. The upper graph of FIG. 6 shows an example of the output signal 21 as a function of time. A predetermined value $S_3$ is indicated in the upper graph. When the output signal 21 falls below the predetermined value $S_3$ (at times $t_{61}$ and $t_{63}$) the fan 3 is switched off in order to reduce the volumetric flow rate of the air flow 4 from the nominal volumetric flow rate $F_n$ to zero. After a predetermined period of time $T_O$, the fan will be switched back on in order to re-establish the nominal volumetric flow rate $F_n$ (at times $t_{62}$, $t_{64}$, and $t_{65}$). If the output signal 21 is still lower than the predetermined value $S_3$ (as measured within the required finite sampling time $T_S$), the fan 3 will again be switched off for a subsequent predetermined period of time $T_O$.

For the embodiment of FIG. 6, the predetermined value $S_3$ preferably corresponds to a sensor signal 21 measured in nominally "clean" air that possesses at most only a relatively small amount of air pollution, thus making a continuous recording of the air pollution not necessary. In this embodiment, the lifetime of the air pollution sensor system 1 is increased as no pollutants will deposit inside the filter 22 during the predetermined periods of time $T_O$ wherein the fan 3 is switched off.

In FIG. 4 and FIG. 6, the volumetric flow rate of the air flow 4 is reduced to zero for a similar predetermined period of time $T_O$. However, it is also possible to have a first predetermined period of time during which the volumetric flow rate is reduced to zero when the output signal 21 exceeds the predetermined value $S_1$, and a second predetermined period of time during which the volumetric flow rate is reduced to zero when the output signal 21 falls below the predetermined value $S_3$, wherein the first predetermined period of time is different from the second predetermined period of time.

The person skilled in the art will understand that the features from the embodiments described hereinbefore can be combined. In this way, an embodiment of the air pollution sensor system 1 can be obtained wherein the fan 3 is arranged to be switched off when the output signal 21 exceeds the predetermined value $S_1$, and also when the output signal 21 falls below the predetermined value $S_3$, thereby defining a range of values for the output signal 21 for which the fan 3 remains switched on, the range having a lower limit of $S_3$ and an upper limit of $S_1$. It would even be possible to use the same value for $S_1$ and $S_3$. In this way, the fan 3 is arranged to be periodically switched on in order to let the sensor unit 2 measure the concentration of airborne pollutants for the required finite sampling time $T_S$, before the fan is switched off again for a predetermined period of time $T_O$.

In the embodiments described hereinbefore, it is convenient to apply a zero reset of the sensor signal 21 during any period of time wherein the fan 3 is switched off, in order to compensate for a possible non-zero offset signal. In case no air passes through the filter 22, the sensor signal 21 should by definition be zero. A non-zero offset signal can arise due to, for instance, temperature variations that affect the electronic circuitry inside the air pollution sensor system 1. The application of a zero reset to the sensor signal 21 at zero volumetric flow rate through the sensor unit 2 also increases the reliability of the sensor signal 21.

While the invention has been illustrated and described in detail in the drawings and foregoing description, such illustration and description are to be considered illustrative or exemplary and not restrictive; the invention is not limited to the disclosed embodiments. Variations to the disclosed embodiments can be understood and effected by those skilled in the art in practicing the claimed invention, from a study of the drawings, the disclosure, and the appended claims. In the claims, the word "comprising" does not exclude other elements, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An air pollution sensor system comprising:
an air inlet,
an air outlet,
a sensor unit, and
an air displacement device arranged to establish an air flow from the air inlet through the sensor unit to the air outlet, the sensor unit comprising a filter for removing airborne pollutants from the air flow, the sensor unit being arranged to generate an output signal based on the amount of airborne pollutants removed from the air flow by the filter, wherein the air displacement device is arranged to reduce the volumetric flow rate of the air flow to a reduced volumetric flow rate of zero in response to the output signal exceeding a predetermined value, and to maintain the air flow at the reduced volumetric flow rate for a predetermined period of time.

2. The air pollution sensor system according to claim 1, wherein the output signal is reset to zero during the predetermined period of time.

3. The air pollution sensor system according to claim 1, wherein the filter is an air-permeable depth filter.

4. The air pollution sensor system according to claim 1, comprising an arrangement for causing the air flow to follow a curved path between the air inlet and the sensor unit.

5. The air pollution sensor system according to claim 1, comprising a heating element that is arranged to reduce the relative humidity of at least a part of the air flow.

6. The air pollution sensor system according to claim 1, wherein the air displacement device is further arranged to adjust the air flow to have an increased volumetric flow rate when the output signal falls below said first predetermined value.

7. An air pollution sensor system comprising:
an air inlet,
an air outlet,
an air displacement device arranged to establish an air flow from the air inlet to the air outlet, and
a sensor comprising a filter for removing airborne pollutants from the air flow, the sensor being arranged to generate an output signal based on an amount of airborne pollutants removed from the air flow by the filter, wherein the air displacement device is arranged to adjust the volumetric flow rate of the air flow to a reduced volumetric flow rate in response to the output signal exceeding a first predetermined value, and to adjust the volumetric flow rate of the air flow to the reduced volumetric flow rate in response to the output signal falling below a second predetermined value.

8. The air pollution sensor system according to claim 7, wherein the air displacement device is further arranged to adjust the air flow to have an increased volumetric flow rate when the output signal falls below said first predetermined value, and to have said increased volumetric flow rate when the output signal exceeds said second predetermined value.

9. The air pollution sensor system according to claim 7, wherein the filter is an air-permeable depth filter.

10. The air pollution sensor system according to claim 7, comprising an arrangement for causing the air flow to follow a curved path between the air inlet and the sensor unit.

11. The air pollution sensor system according to claim 7, comprising a heating element that is arranged to reduce the relative humidity of at least a part of the air flow.

12. The air pollution sensor system according to claim 7, wherein the air displacement device is further arranged to adjust the air flow to have an increased volumetric flow rate when the output signal falls below said first predetermined value.

* * * * *